US00PP17648P3

(12) United States Plant Patent
Thomsen

(10) Patent No.: US PP17,648 P3
(45) Date of Patent: Apr. 24, 2007

(54) ***EUPHORBIA* PLANT NAMED 'HJOR045'**

(50) Latin Name: ***Euphorbia milii* Desmoul.×*Euphorbia lophogona* Lam.**
Varietal Denomination: HJOR045

(75) Inventor: Steen J. Thomsen, Sonderso (DK)

(73) Assignee: Hjortebjerg Plant Licence A/S, Sonderso (DK)

( * ) Notice: Subject to any disclaimer, the term of this patent is extended or adjusted under 35 U.S.C. 154(b) by 0 days.

(21) Appl. No.: 11/236,826

(22) Filed: Sep. 28, 2005

(65) Prior Publication Data

US 2006/0085879 P1 Apr. 20, 2006

(30) Foreign Application Priority Data

Oct. 15, 2004 (QZ) ..... PBR 20041908

(51) Int. Cl.
*A01H 5/00* (2006.01)

(52) U.S. Cl. ..... Plt./302
(58) Field of Classification Search ..... Plt./302
See application file for complete search history.

(56) References Cited

PUBLICATIONS

McLaughlin, A Word or Two About Gardening From Africa via Thailand Comes Some Low–Maintenance Garden Color, 2002, University of Florida IFAS Extension [online], [retrieved on Jun. 9, 2006]. Retrieved from the Internet <http://miami–dade.ifas.ufl.edu/programs/urbanhort/publications/A–Word–or–Two–II.htm> 4 pages.*

Upov–rom GTITM Plant Variety Database, 2006/01, GTI Jouve Retrieval Software, Citation for *Euphorbia* '2004–5', one page.*

* cited by examiner

*Primary Examiner*—Kent Bell
*Assistant Examiner*—June Hwu
(74) *Attorney, Agent, or Firm*—Foley & Lardner LLP

(57) ABSTRACT

A new distinct cultivar of *Euphorbia* plant named 'HJOR045', characterized by its compact plant habit; very dense and bushy plant form, mainly due to upright stems; large number of long stemmed flowers per plant due to 9 to 14 cm in length reddish peduncles; colored bracts of red, RHS 54B, with an apical margin spot of RHS 138B, green; and large, oblanceolate, yellow-green leaves with reddish-purple margins and abaxial side.

3 Drawing Sheets

Botanical designation: *Euphorbia milii* Desmoul.×*Euphorbia lophogona* Lam.
Variety denomination: 'HJOR045'.

BACKGROUND OF THE INVENTION

The present Invention relates to a new and distinct cultivar of *Euphorbia* plant, botanically known as *Euphorbia milii* Desmoul.×*Euphorbia lophogona* Lam., commonly known by the name Crown of Thorns, and hereinafter referred to by the name 'HJOR045'.

The new *Euphorbia* cultivar is a product of a planned breeding program conducted by the Inventor, Steen Thomsen, in Haarslev, Fyn, Denmark. The new *Euphorbia* cultivar originated from a cross made in November of 2003 by the Inventor between an unnamed, unpatented seedling plant of an *Euphorbia milii* Desmoul. cultivar and an unnamed, unpatented seedling plant of an *Euphorbia lophogona* Lam. cultivar. The Inventor selected the new *Euphorbia* cultivar as a single flowering plant from the progeny of the above crossing in January of 2004 on the basis of its flower color combination, large leaves and upright, compact plant habit. Plants of the new *Euphorbia* cultivar have upright and compact plant habit, and produce large, abundant inflorescence with a unique color combination of red and green.

Asexual reproduction of the new cultivar was first performed in January of 2004 by terminal cuttings, and propagation in trial production batches in Hjortebjerg, Denmark, has demonstrated that the combination of unique features as disclosed herein for this new *Euphorbia* cultivar are firmly fixed and retained through successive generations of asexual reproduction. The new cultivar reproduces true-to-type.

BRIEF SUMMARY OF THE INVENTION

The following traits have been repeatedly observed and are determined to be the unique characteristics of 'HJOR045'. These characteristics in combination distinguish 'HJOR045' as a new and distinct *Euphorbia* cultivar:

1. Upright, compact plant habit;
2. Very dense and bushy plant form, mainly due to upright stems;
3. Large number of long stemmed flowers per plant due to 9 to 14 cm in length reddish peduncles;
4. Colored bracts of red, RHS 54B, with an apical margin spot of RHS 138B, green; and
5. Large, oblanceolate, yellow-green leaves, RHS 146B–D, with reddish-purple margins and abaxial side, RHS 71B.

Plants of the new *Euphorbia* cultivar 'HJOR045' differ from plants of the parental cultivars, an unnamed, unpatented seedling plant of an *Euphorbia milii* Desmoul. and an unnamed, unpatented seedling plant of an *Euphorbia lophogona* Lam. cultivar, primarily by floral bract and leaf size and color. Plants of 'HJOR045' produce bright red bracts (with a green spot) on long peduncles and large, yellow-green leaves with reddish-purple margins. In addition, plants of 'HJOR045' have more proliferate flowering than the parental cultivars.

Plants of the cultivar 'HJOR045' can be compared to plants of the *Euphorbia milii* cultivar 'Themis' (unpatented). In side-by-side comparisons conducted by the Inventor in Haarslev, Denmark, plants of the new cultivar 'HJOR045' and the comparison cultivar 'Themis' differ in the following characteristics:

1. Plants of 'HJOR045' are shorter and more compact than plants of 'Themis';
2. Plants of 'HJOR045' have striking a color combination of red bracts, RHS 54A to RHS 54B, orange staminate cyathia, RHS N25B, with orange-red glands, RHS 31B, whereas plants of 'Themis' have a striking color combination of red bracts, RHS 41C, staminate cyathia with RHS 154B to RHS 154A and an edge of orange, RHS 34B;
3. Plants of 'HJOR045' have large, oblanceolate, yellow-green colored leaves, with reddish-purple margins and undersides, whereas plants of 'Themis' have dark green leaves;
4. Plants of 'HJOR045' have longer and sturdier petioles than plants of 'Themis';
5. During the life cycle, plants of 'HJOR045' produce more inflorescences and buds per plant than plants of 'Themis'; and
6. Plants of 'HJOR045' have shorter and wider inflorescence than the plants of 'Themis'.

BRIEF DESCRIPTION OF THE PHOTOGRAPHS

The accompanying color photographs illustrate the overall appearance and details of flower form, color and structures of the new cultivar 'HJOR045', showing the colors as true as it is reasonably possible to obtain in color reproductions of this type. Colors in the photographs may differ slightly from the color values cited in the detailed botanical description, which more accurately describe the actual colors of the new *Euphorbia* cultivar.

DETAILED BOTANICAL DESCRIPTION

Figure 1:
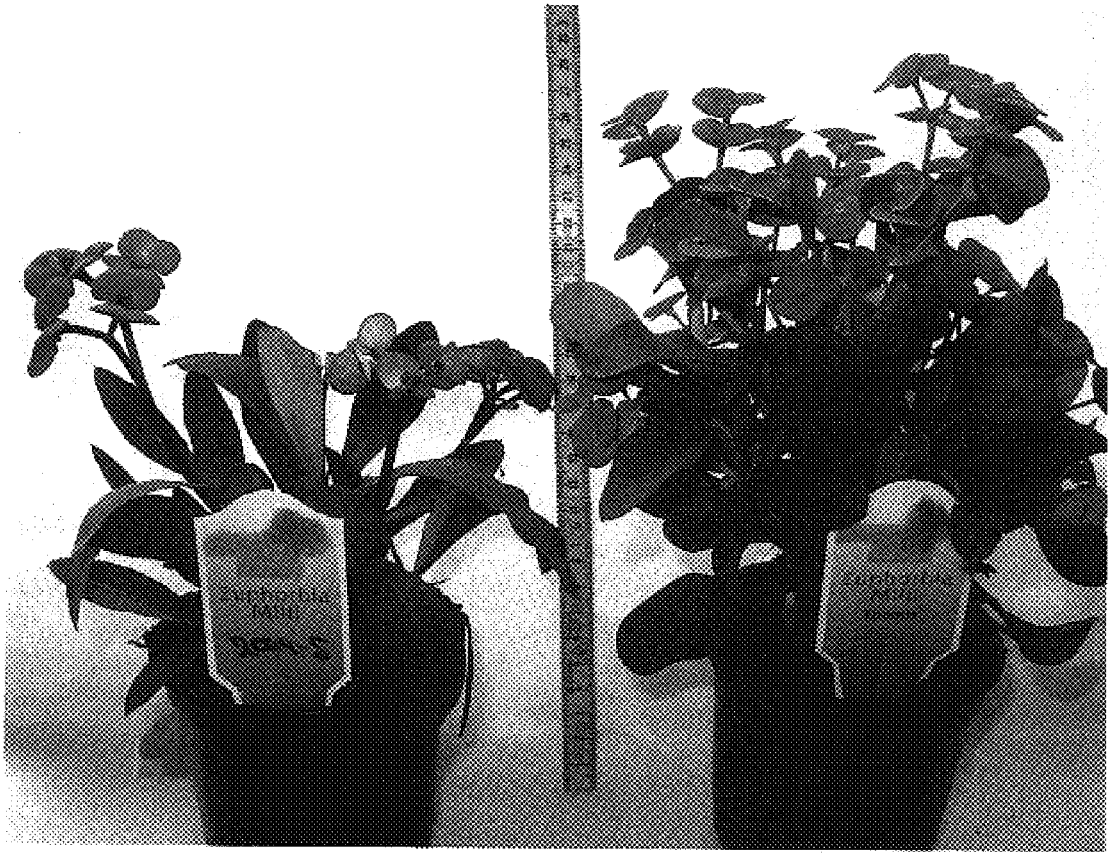
FIG. 1 shows a side view perspective comparing a typical, potted flowering plant of the new cultivar 'HJOR045' (on the left, identified by the Breeder's Reference 2004-5) to a typical, potted flowering plant of the comparison cultivar 'Themis' (on the right), both grown in 11 cm pots.
Figure 2:
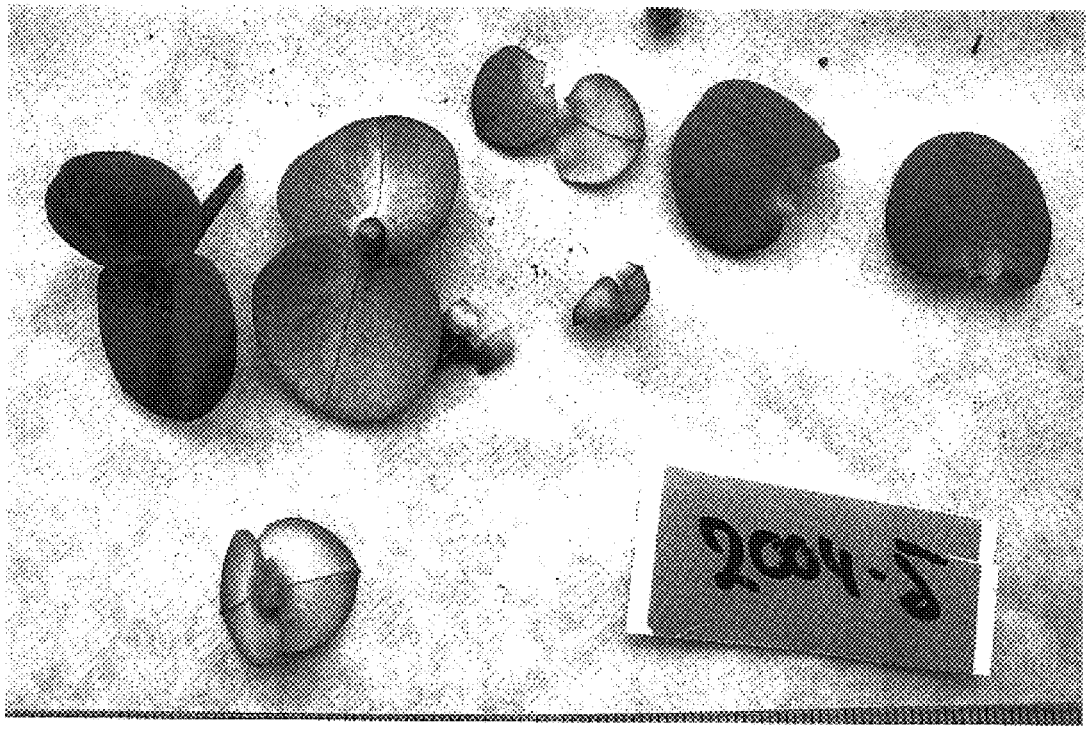
FIG. 2 shows a close-up view of young and mature floral cymes of a typical flowering plant of the new cultivar 'HJOR045' (identified by the Breeder's Reference 2004-5).
Figure 3:
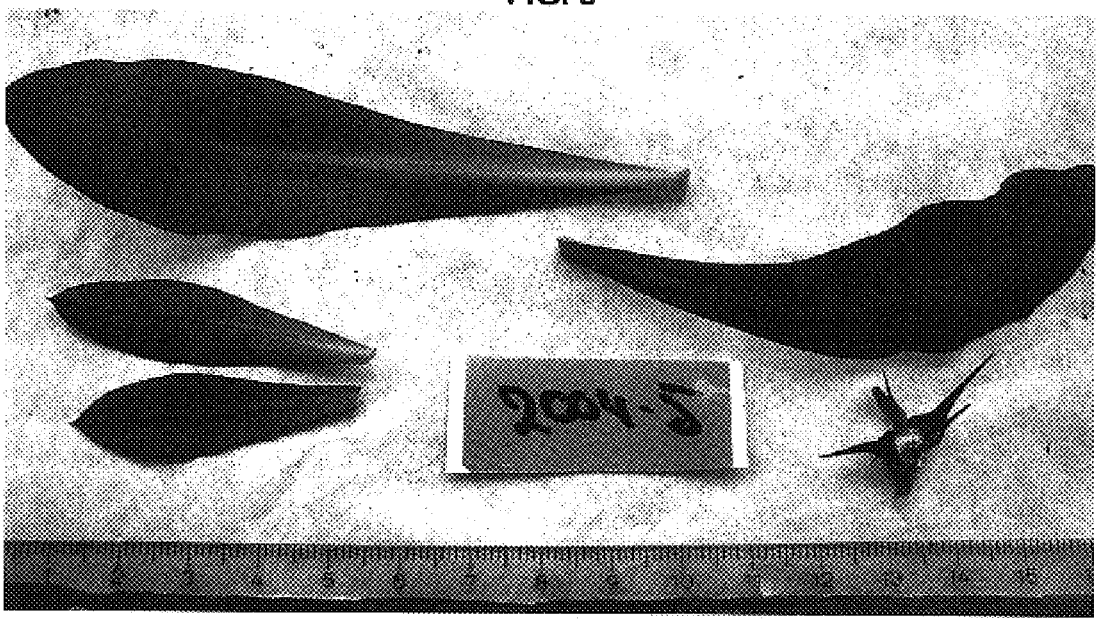
FIG. 3 shows a close-up view of different size leaves and thorns of a typical flowering plant of the new cultivar 'HJOR045' (identified by the Breeder's Reference 2004-5).

Plants of the new cultivar 'HJOR045' have not been observed under all possible environmental conditions. The phenotype may vary somewhat with variations in environment such as temperature, light intensity, day length, and fertility level without, however, any variance in genotype.

The aforementioned photographs, together with the following observations, measurements and values describe plants of the new cultivar 'HJOR045' as grown in a glass greenhouse in Fyn, Denmark, under conditions which closely approximate those generally used in commercial practice. Plants of 'HJOR045' were grown in a greenhouse with the day temperature range of 21° C. to 24° C. and the night temperature range of 20° C. to 21° C. Plants of 'HJOR045' were grown in full light, and no photoperiodic treatments or growth retardants were used. For flower induction, plants of 'HJOR045' are subjected to high irradiance conditions and a constant temperature of 24° C.

Color references are made to The Royal Horticultural Society Colour Chart (R.H.S.), 4$^{th}$ edition, except where general terms of ordinary dictionary significance are used. Plants used for this description were grown for about 17 weeks after cutting and produced in 6 cm pots. Other pot sizes can be used and the plants are intended for indoor use or as a bedding plant in temperature climates while it is a perennial garden plant in tropical and subtropical areas.

Botanical classification: *Euphorbia milii* Desmoul.× *Euphorbia lophogona* Lam.

Parentage:

*Female or seed parent.*—Unnamed, unpatented seedling plant of *Euphorbia milii* Desmoul.

*Male or pollen parent.*—Unnamed, unpatented seedling plant of *Euphorbia lophogona* Lam.

Propagation:

*Type cutting.*—Terminal vegetative cuttings taken from plants kept in the vegetative stage by shading and high temperatures (25° C.).

*Time to initiate roots.*—About 10 to 14 days at 18° C. to 21° C. in tunnels in a greenhouse.

*Root description.*—Fine, fibrous, well branched.

*Root color.*—White, RHS 158B.

Plant description:

*Form.*—Perennial plant with upright plant habit. 'HJOR045' flowers in cymes with 5 cyathia subtended by 5 glands and 2 colored bracts.

*Crop time.*—After rooting, about 16 to 18 weeks are required to produce finished flowering plants in 11 cm pots.

*Vigor.*—Moderately vigorous growth rate.

*Plant size.*—Height (soil level to top of plant plane): About 13 cm. Width: About 16 cm.

Lateral branches: Freely branching with about 3 lateral flowering branches forming at every node; dense and bushy. Lateral branches measure between 2 to 3 cm in length and about 5 mm in diameter. Internode length measures about 6 mm. About 2 to 4 buds per lateral stem and about 4 to 6 flowers per lateral stem. Stems are square to pentagonal with thorned ridges — about 15 mm thick at the base. Young stem color is yellow-green, RHS 144A, and older stems are gray-green, RHS 194A. By each node appears a group of thorns: 1 large (16 mm) and 1 small (4 mm). Young thorns are soft and gray-purple, RHS 187A, while the older thorns becomes stiffer and change color to brown, RHS 187C.

Foliage description: Leaves alternate, single, oblanceolate in shape, entire margin (undulating when foliage young), and costate pinnipalmate venation. Length: 11 cm. Width: About 25 mm. Apex: Mucronate. Base: Cuneate to almost decurrent. Texture: smooth, waxy, dull, and glabrous. Color: Young foliage: (upper side): Yellow-green, RHS 146B, with red-purple edges, RHS 71B; (under side): Yellow-green, RHS 146D, with red-purple edges, RHS 71B. Mature foliage: (upper side): Yellow-green, RHS 139A; (under side): Yellow-green, RHS 138B, with intercoastal mottling color of red-purple, RHS 71C. Venation pattern: Costate, pinnipalmate. Venation color: (upper side): Yellow-green, RHS 138B; (under side): Gray-purple, RHS N187B. Petiole length: About 10 mm. Petiole diameter: About 1 mm. Petiole color: Gray-green, RHS 195A.

Flower description:

*Flower arrangement and shape.*—Floral arrangements composed of dichasial cymes. The flowers (cyathia) are starkly reduced so only a circle of 5 glands and the reproductive organs are present. Subtending the cyathia are two colored bracts. The flowers are further complicated by the unique feature of funnel shaped floral buds appearing at the base of the bracts in two or more layers.

*Natural flowering season.*—Continuous throughout the spring and summer in subtropical and tropical regions. In colder climates season, can be extended by greenhouse production with high temperatures and supplementary irradiance.

*Flower longevity on the plant.*—About 5 to 9 weeks. However, longevity of individual flowers is highly dependent on temperature and light conditions. Bracts turn green with age. Entire cymes drop after withering.

*Rate of flower opening.*—About 1 to 4 per week.

*Fragrance.*—None.

*Inflorescence size.*—Diameter: About 4×7 cm. Height: 4 to 5 cm.

*Buds.*—Funnel shape, measures about 4 mm in length and about 2 mm in diameter, color: yellow-green, RHS 150C, with red-purple edges, RHS 63A.

*Flowers.*—Round shape, aspect of about 45° to 60°, about 2 mm in diameter and about 1 mm in height (depth).

*Bracts.*—2, opposite, partly overlapping at base, cordate shape with obtuse tip, average 13 mm in length and about 22 mm in width, color when opening: (upper side) red, RHS 54B; (underside) yellow-green, RHS 150C, with red edges, RHS 54C, color when fully opened: (upper side): red, RHS 54A, with a green, RHS 138A, triangular spot developing at apex; (under side) light yellow-green, RHS 150C, with red edges, RHS 54C.

*Glands.*—Flower (cyanthium) subtended by 5 conspicuous glands. Color from orange, RHS N25B, to orange-red, RHS 31B, during development.

*Peduncles.*—Length measuring from 9 to 14 cm, diameter measuring about 3 mm, angle about 45°, soft in strength, color: gray-red, from RHS 181A to RHS 181B.

*Pedicel.*—Length measuring from 1 to 4 cm, diameter measuring about 1 mm, angle about 45°, strong in strength, color: gray-red, RHS 181B.

Reproductive organs:

*Androecium.*—Stamen: 5 (appears after flower matures). Anthers: Globular shape measuring about 1 to 2 mm, yellow-orange color, RHS 15A. Pollen: Plentiful, yellow-orange color, RHS 15A.

*Gynoecium.*—Pistil: Appears before cyathia mature; one, tripartite pistil measuring about 2 mm in length; stigma tripartite with split ends, and color RHS 1C, greenish-yellow; style measuring about 1 to 3 mm in length and color, RHS 1D, greenish-yellow; ovary color, RHS 149D, yellow-green.

*Seeds/fruit.*—None observed.

Weather tolerance: Plants of the new *Euphorbia* cultivar have exhibited good tolerance to drought, rain and wind; however, flowering may cease during cold and dark periods when temperatures are below +15° C.

Pest/disease tolerance/susceptibility: Plants of the new *Euphorbia* cultivar have exhibited good tolerance to following fungi: powdery mildew and *Thielaviopsis* (a root rot fungus). Also, they appear to be less infected by Thrips (*Frankliniella*).

I claim:

1. A new and distinct cultivar of *Euphorbia* plant named 'HJOR045', as illustrated and described herein.

* * * * *